(12) United States Patent
Chapman et al.

(10) Patent No.: US 8,417,327 B2
(45) Date of Patent: Apr. 9, 2013

(54) VARIABLE FREQUENCY IMPEDANCE MEASUREMENT

(75) Inventors: Fred W. Chapman, Renton, WA (US); Joseph L. Sullivan, Kirkland, WA (US); Scott O. Schweizer, Snohomish, WA (US)

(73) Assignee: Physio-Control, Inc., Redmond, WA (US)

( * ) Notice: Subject to any disclaimer, the term of this patent is extended or adjusted under 35 U.S.C. 154(b) by 2214 days.

(21) Appl. No.: 10/176,705

(22) Filed: Jun. 20, 2002

(65) Prior Publication Data

US 2003/0236468 A1 Dec. 25, 2003

(51) Int. Cl.
*A61B 5/05* (2006.01)

(52) U.S. Cl.
USPC .......... 600/547; 600/548; 607/7; 607/8; 607/28

(58) Field of Classification Search .......... 607/28, 607/7–8; 600/547–548
See application file for complete search history.

(56) References Cited

U.S. PATENT DOCUMENTS

| | | |
|---|---|---|
| 3,747,605 A | 7/1973 | Cook |
| 3,789,834 A | 2/1974 | Duroux |
| 4,574,810 A | 3/1986 | Lerman |
| 4,771,781 A | 9/1988 | Lerman |
| 4,780,661 A | 10/1988 | Bolomey et al. |
| 4,825,870 A | 5/1989 | Mann et al. |
| 4,840,177 A | 6/1989 | Charbonnier et al. |
| 4,917,093 A * | 4/1990 | Dufresne et al. .......... 607/62 |
| 5,088,489 A | 2/1992 | Lerman |
| 5,092,339 A * | 3/1992 | Geddes et al. .......... 600/505 |
| 5,099,856 A | 3/1992 | Killion et al. |
| 5,111,813 A * | 5/1992 | Charbonnier et al. .......... 607/8 |
| 5,203,344 A | 4/1993 | Scheltinga et al. |
| 5,230,336 A * | 7/1993 | Fain et al. .......... 607/7 |
| 5,284,136 A | 2/1994 | Hauck et al. |
| 5,395,373 A * | 3/1995 | Ayers .......... 607/8 |
| 5,503,157 A | 4/1996 | Sramek |
| 5,534,015 A | 7/1996 | Kroll et al. |
| 5,540,722 A | 7/1996 | Clare et al. |
| 5,540,723 A | 7/1996 | Ideker et al. |
| 5,593,427 A | 1/1997 | Gliner et al. |
| 5,601,612 A | 2/1997 | Gliner et al. |
| 5,607,454 A | 3/1997 | Cameron et al. |

(Continued)

FOREIGN PATENT DOCUMENTS

| | | |
|---|---|---|
| EP | 0 570 895 A2 | 11/1993 |
| EP | 1 027 860 A1 | 8/2000 |
| WO | WO 99/29369 | 6/1999 |

OTHER PUBLICATIONS

Geddes et al., "The prediction of the impedance of the thorax to defibrillating current," Medical Instrumentation, vol. 10, No. 3, pp. 159-162, May-Jun. 1976.

*Primary Examiner* — Deborah Malamud
(74) *Attorney, Agent, or Firm* — Marger Johnson & McCollom PC

(57) ABSTRACT

When a defibrillator selects a dosage of energy or current to be delivered to a patient, the defibrillator selects an excitation current frequency and applies the excitation current at the selected frequency to the patient. The frequency of the excitation current is selected as a function of the dosage to be delivered. The patient's response to the excitation current at the selected frequency will accurately reflect the impedance that the defibrillator will "see" when delivering the selected dosage of energy or current.

16 Claims, 5 Drawing Sheets

U.S. PATENT DOCUMENTS

| | | | |
|---|---|---|---|
| 5,632,267 A | | 5/1997 | Hognelid et al. |
| 5,662,687 A | | 9/1997 | Hedberg et al. |
| 5,735,883 A | * | 4/1998 | Paul et al. ................ 607/28 |
| 5,755,742 A | | 5/1998 | Schuelke et al. |
| 5,824,029 A | * | 10/1998 | Weijand et al. ............. 607/122 |
| 5,836,978 A | | 11/1998 | Gliner et al. |
| 5,902,324 A | | 5/1999 | Thompson et al. |
| 5,974,339 A | * | 10/1999 | Baker et al. ................ 607/7 |
| 5,999,852 A | | 12/1999 | Elabbady et al. |
| 6,047,212 A | | 4/2000 | Gliner et al. |
| 6,058,325 A | | 5/2000 | Baura |
| 6,058,327 A | | 5/2000 | Borgerding et al. |
| 6,076,015 A | * | 6/2000 | Hartley et al. ............. 607/20 |
| 6,101,413 A | * | 8/2000 | Olson et al. ............... 607/5 |
| 6,134,468 A | | 10/2000 | Morgan et al. |
| 6,198,967 B1 | | 3/2001 | Brewer et al. |
| 6,241,751 B1 | | 6/2001 | Morgan et al. |
| 6,304,783 B1 | | 10/2001 | Lyster et al. |
| 6,400,984 B1 | | 6/2002 | Medema |
| 6,405,081 B1 | * | 6/2002 | Lyster et al. ............... 607/5 |
| 6,522,924 B1 | * | 2/2003 | Meier ...................... 607/28 |
| 6,604,002 B2 | * | 8/2003 | Molin ...................... 607/28 |
| 6,647,290 B2 | * | 11/2003 | Wuthrich ................... 607/5 |
| 6,650,936 B2 | * | 11/2003 | Sullivan et al. ............. 607/6 |
| 6,907,290 B2 | * | 6/2005 | Legay ..................... 607/28 |
| 2003/0032989 A1 | * | 2/2003 | Herleikson ................. 607/8 |
| 2003/0195580 A1 | * | 10/2003 | Bradley et al. ............. 607/28 |

* cited by examiner

VARIABLE FREQUENCY IMPEDANCE MEASUREMENT

TECHNICAL FIELD

The invention relates to medical devices, and more particularly, to defibrillators that deliver energy to a patient.

BACKGROUND

A defibrillator is a device that stores energy, typically in one or more high-voltage capacitors, and delivers the stored energy to a patient. In particular, a defibrillator delivers energy to a heart that is undergoing fibrillation and has lost its ability to contract. Ventricular fibrillation is particularly life threatening because activity within the ventricles of the heart is so uncoordinated that virtually no pumping of blood takes place. An electrical pulse delivered to a fibrillating heart may depolarize the heart and cause it to reestablish a normal sinus rhythm. For some patients, more than one defibrillation pulse is required.

An external defibrillator applies a defibrillation pulse via electrodes placed upon the patient's chest. When a switch is closed, current flows between the electrodes and the defibrillator delivers at least some of the stored energy to the patient's chest. The dosage of energy delivered may be on the order of two hundred joules or more, but the dosage depends upon the circumstances. The quantity of energy delivered when the patient is a child, for example, is generally less than when the patient is an adult. In some cases, a patient may need multiple shocks, and different dosages may be delivered with each shock.

The energy delivered to the patient, and the current that flows between the electrodes, are a function of the voltage between the electrodes, the impedance of the body of the patient and the pulse width of the shock. For a given voltage and pulse width, a patient having a body with a lower impedance will experience a different current flow, and will thus receive a different quantity of energy, than a patient having a body with a higher impedance. A defibrillator that measures the patient's impedance accurately can therefore more effectively develop a voltage across the electrodes that accurately delivers a desired dosage of energy or current to the patient. A defibrillator that measures the patient's impedance accurately can also adjust the shape of the pulse for enhanced effect.

A defibrillator may measure the impedance of the patient's body by applying an excitation current, or "carrier," to the patient via the electrodes placed upon the patient's chest, and measuring the response to the application of the excitation current via the electrodes. The response is typically measured as a function of the voltage difference between the electrodes.

The excitation current is an alternating current signal, having a small current magnitude, such as 100 microamperes, and a known frequency. By measuring the magnitude and phase of the response, the patient's impedance can be determined. Because the patient's body is not purely resistive but includes a reactive component, the measured impedance varies depending upon the frequency of the excitation current. Defibrillators that measure impedance with an excitation current typically employ one or two particular fixed frequencies, such as 20 kHz, 30 kHz or 62 kHz.

The excitation current does not deliver the defibrillation shock. A typical defibrillation shock is of a substantially higher amperage than the excitation current. During delivery of defibrillation shocks, the impedance exhibited by the patient and "seen" by the defibrillator varies. Impedance varies from patient to patient, and may also vary within a single patient as a function of factors such as the magnitude of the defibrillation shock. The impedance exhibited by the patient during delivery of a defibrillation shock may not be the same as the impedance exhibited during measurement of the response to the excitation current.

SUMMARY

The invention provides techniques for accurately estimating the amount of impedance that a patient will exhibit when a defibrillator delivers a dosage of energy or current to the patient. When the defibrillator selects a dosage to be delivered to the patient, the defibrillator measures the impedance of the patient by observing the response to application of an excitation current. The defibrillator selects an excitation current frequency that will accurately reflect the impedance that the patient will exhibit when the defibrillator delivers the selected dosage.

In one embodiment, the invention is directed to a method in which a frequency of an excitation current is selected as a function of a dosage of energy or current to be delivered to a patient with a defibrillator. The method includes applying the excitation current to the patient at the selected frequency. The impedance of the patient may be measured by measuring a response of the patient to application of the excitation current.

In another embodiment, the invention is directed to a defibrillator comprising a processor that selects a dosage of energy or current to be delivered to a patient and a current source that generates an excitation current at a selectable frequency, the frequency of the excitation current being a function of the selected dosage. The defibrillator may also include electrodes that deliver the excitation current to the patient and an impedance measuring circuit that measures the voltage across the electrodes and measures the impedance as a function of the voltage and the excitation current.

In a further embodiment, the invention presents a method comprising applying an excitation current of at least two different frequencies to a patient. The method also includes measuring the impedances of the patient by measuring the responses of the patient to application of the excitation current at the different frequencies. The method further includes selecting the second frequency as a function of the first measured impedance and as a function of a dosage of energy or current to be delivered to the patient.

In an additional embodiment, the invention presents a defibrillator comprising a current source that generates an excitation current at a selectable frequency, electrodes that deliver the excitation current to the patient at a selected frequency, an impedance measuring circuit that measures the voltage across the electrodes and measures an impedance as a function of the voltage and the excitation current and a processor that selects the selected frequency of the excitation current as a function of a dosage of energy or current to be delivered to the patient. The processor may also select the dosage.

The invention can provide one or more advantages, including techniques for more accurate and effective delivery of a dosage of energy or current. By selecting an excitation current frequency as a function of the dosage to be delivered, the defibrillator may obtain data that will allow the defibrillator to charge the energy storage device to a voltage level that will accurately deliver the selected dosage. In this manner, the defibrillator is capable of more accurate dosage delivery and therapy and more accurate determination of patient impedance. Furthermore, the invention may complement and cooperate with other impedance-related measurements, such as measurement of body motion or detection of an improperly applied electrode.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
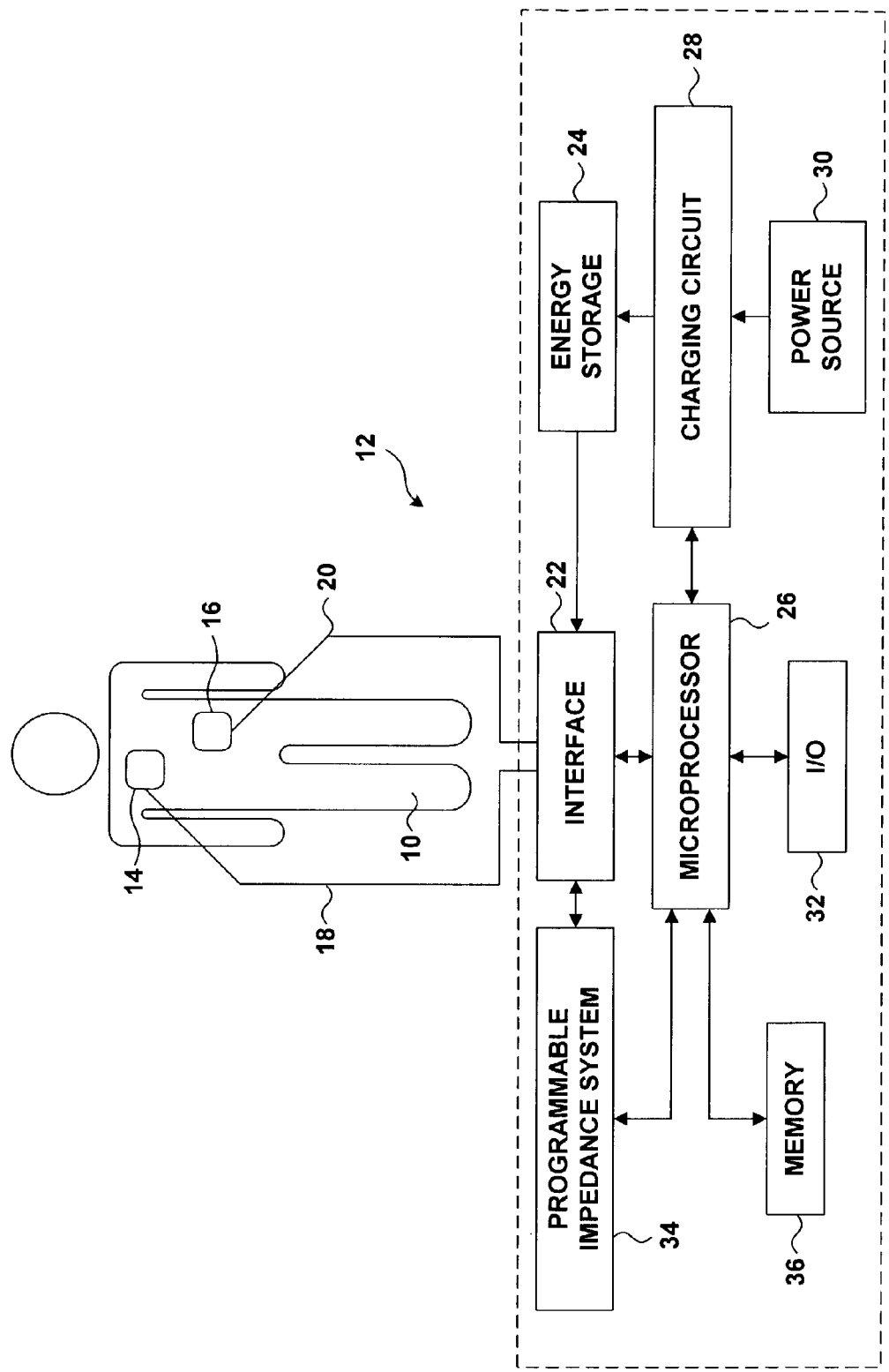
FIG. 1 is a schematic diagram of an external defibrillator and a patient.

FIG. 1 is a block diagram showing a patient 10 coupled to an external defibrillator 12. Defibrillator 12 administers defibrillation therapy to patient 10 via electrodes 14 and 16, which may be hand-held electrode paddles or adhesive electrode pads placed on the skin of patient 10. The body of patient 10 provides an electrical path between electrodes 14 and 16.

Electrodes 14 and 16 are coupled to defibrillator 12 via conductors 18 and 20 and interface 22. In a typical application, interface 22 includes a receptacle, and connectors 18, 20 plug into the receptacle. Electrical impulses or signals may be sensed by defibrillator 12 via electrodes 14 and 16 and interface 22. Electrical impulses or signals may also be delivered from defibrillator 12 to patient 10 via electrodes 14 and 16 and interface 22.

Interface 22 includes a switch (not shown in FIG. 1) that, when activated, couples an energy storage device 24 to electrodes 14 and 16. Energy storage device 24 stores the energy for a dosage of energy or current to be delivered to patient 10. The switch may be of conventional design and may be formed, for example, of electrically operated relays. Alternatively, the switch may comprise an arrangement of solid-state devices such as silicon-controlled rectifiers or insulated gate bipolar transistors.

Energy storage device 24 includes components, such one or more capacitors, that store the energy to be delivered to patient 10 via electrodes 14 and 16. Before a defibrillation pulse may be delivered to patient 10, energy storage device 24 must be charged. A microprocessor 26 directs a charging circuit 28 to charge energy storage device 24 to a high voltage level. Charging circuit 28 comprises, for example, a flyback charger that transfers energy from a power source 30 to energy storage device 24. Because the life of patient 10 may depend upon receiving defibrillation, charging should take place rapidly so that the defibrillation shock may be delivered with little delay.

When the energy stored in energy storage device 24 reaches the desired level, defibrillator 12 is ready to deliver the defibrillation shock. The shock may be delivered automatically or manually. When the shock is delivered automatically, microprocessor 26 activates an input/output (I/O) device 32, such as an indicator light or a voice prompt, that warns the operator that defibrillator 12 is ready to deliver a defibrillation shock to patient 10. The warning informs the operator of the impending shock so that no one other than patient 10 will receive the defibrillation shock. Microprocessor 26 then activates the switch to electrically connect energy storage device 24 to electrodes 14 and 16, and thereby deliver a defibrillation shock to patient 10. In the case of a manual delivery, microprocessor 26 may activate an I/O device 32 that informs the operator that defibrillator 12 is ready to deliver a defibrillation shock to patient 10. The operator may activate the switch by manual operation, such as pressing a button, and thereby deliver a defibrillation shock to patient 10.

Microprocessor 26 may also modulate the electrical pulse delivered to patient 10. Microprocessor 26 may, for example, regulate the shape of the waveform of the electrical pulse and the duration of the pulse.

Microprocessor 26 may perform other functions as well, such as monitoring electrocardiogram (ECG) signals sensed via electrodes 14 and 16 and received via interface 22. Microprocessor 26 may determine whether patient 10 suffers from a condition that requires a defibrillation shock, based upon the ECG signals. In addition, microprocessor 26 may also evaluate the efficacy of an administered defibrillation shock, determine whether an additional shock is warranted, and the magnitude of energy to be delivered in the additional shock.

The goal of defibrillation is to depolarize the heart with electrical current and cause the heart to reestablish a normal sinus rhythm. In some patients, one shock is insufficient to reestablish normal rhythm, and one or more additional defibrillation shocks may be required. Before another shock may be administered, however, charging circuit 28 ordinarily must transfer energy from power source 30 to energy storage device 24, thereby recharging energy storage device 24. In recharging energy storage device 24, as in the initial charging, time is of the essence, and charging circuit 28 therefore charges energy storage device 24 quickly. The energy or current dosage delivered to patient 10 need not be the same in each shock.

Power source 30 may comprise, for example, batteries and/or an adapter to an exterior power source such as an electrical outlet. In addition to supplying energy to charging circuit 28 and energy storage device 24, power source 30 also supplies power to components such as microprocessor 26 and I/O device 32, e.g., via a power supply circuit (not shown in FIG. 1).

Defibrillator 12 further includes programmable impedance system 34. As will be described in more detail in connection with FIG. 2, programmable impedance system 34 includes a controllable current source for generating an "excitation current," also called a "carrier." The excitation current is applied to patient 10 through interface 22 and electrodes 14 and 16. Programmable impedance system 34 also includes an impedance measuring circuit that measures the impedance of the body of patient 10 via electrodes 14 and 16 and interface 22. The impedance measuring circuit detects the response to the excitation current as a time-varying voltage difference between electrodes 14 and 16. By measuring the magnitude and phase of the voltage difference, programmable impedance system 34 measures the impedance of patient 10.

The excitation current may be an alternating current signal of known magnitude and frequency. The excitation current is much smaller in magnitude than the defibrillation current delivered during delivery of an energy or current dosage. A typical excitation current has a magnitude of around 100 microamperes. When applied to patient 10, the excitation current is typically constant in magnitude and frequency during the period of application. The frequency of the excitation current may be varied, however, and the frequency employed during one period may be different from the frequency employed during another period. For example, programmable impedance system 34 may, during a first period, apply an excitation current to patient 10 with a constant frequency of 30 kHz. During a later period, the programmable impedance system 34 may apply an excitation current to patient 10 with a constant frequency of 60 kHz.

The impedance measured using an excitation current at one frequency will usually not be the same as the impedance measured using an excitation current at a different frequency. A human body demonstrates both resistive and reactive components, so the measured impedance of patient 10 varies depending upon the frequency of the excitation current.

Impedance measurements may be stored in memory 36. Memory 36 may store other data as well, such as vital signs of patient 10 and the therapy delivered to patient 10. In addition, memory 36 may store instructions that direct the operation of microprocessor 26. Memory 36 may include volatile storage, such as random access memory, and/or non-volatile storage, such as flash memory or a hard disk.

In one embodiment of the invention, programmable impedance system 34 selects a frequency for the excitation current as a function of the energy or current to be delivered to patient 10 in a pending defibrillation shock. The energy or current dosage delivered in a defibrillation shock is a function of the voltage difference across electrodes 14 and 16 and the impedance of patient 10 between electrodes 14 and 16. The impedance of patient 10, however, varies as a function of the magnitude of the defibrillation pulse.

In defibrillation, the energy delivered to patient 10, rather than the voltage difference developed across electrodes 14 and 16, is usually the quantity of interest. The energy delivered to patient 10 varies with the current delivered via electrodes 14 and 16, and so defibrillation may also be quantified in terms of the delivered current. For purposes of simplicity, the invention will be described in terms of a dosage of energy, but the invention encompasses dosages of current as well.

To deliver a desired dosage of energy with reasonable accuracy, therefore, the impedance of patient 10 should be measured with reasonable accuracy, and the measured impedance should be close to the impedance that defibrillator 12 will see when delivering the defibrillation shock. Defibrillator 12 may then control the voltage across electrodes 14 and 16 to deliver the desired dosage of energy, and may also control the waveform of the electrical pulse and the duration of the pulse. The invention provides techniques for selecting a frequency for the excitation current that will accurately reflect the impedance that patient 10 will exhibit and that defibrillator 12 will see when delivering the defibrillation shock. With this feature, defibrillator 12 can be controlled to avoid delivering a dosage of energy that is too high or too low for desired effectiveness.

Figure 2:
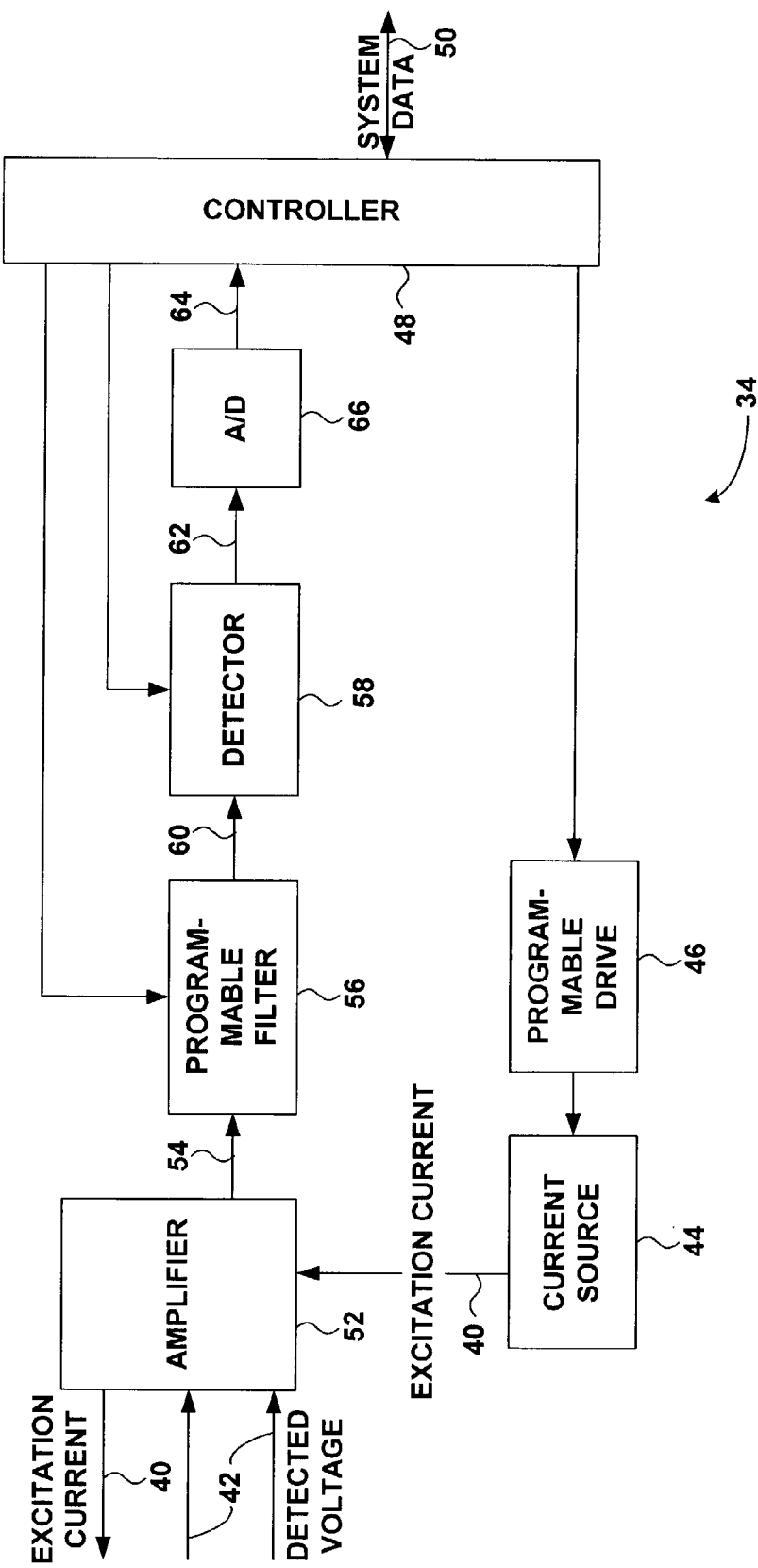
FIG. 2 is a block diagram illustrating an exemplary embodiment of a programmable impedance system.

FIG. 2 is a block diagram illustrating an exemplary embodiment of programmable impedance system 34. Programmable impedance system 34 supplies an excitation current 40 to interface 22 (not shown in FIG. 2). A voltage 42 across electrodes 14 and 16 (not shown in FIG. 2) is an input to programmable impedance system 34.

Excitation current 40 is supplied by a controlled current source 44. Current source 44 is controlled by a programmable drive 46, which regulates the frequency of excitation current 40. Controller 48 selects the frequency of excitation current 40 and supplies the selected frequency to programmable drive 46. Current source 44 may generate excitation current 40 along a continuous range of frequencies, or may generate excitation current 40 at discrete frequencies. In a typical application, current source 44 may generate excitation current 40 at three or more frequencies, and controller 48 may select the frequency of excitation current 40 from at least three frequencies.

In one embodiment of the invention, controller 48 selects the frequency of excitation current 40 as a function of the dosage of energy to be delivered to patient 10 in a pending defibrillation shock. The energy to be delivered is one element of system data 50 that may be supplied to programmable impedance system 34.

Programmable impedance system 34 supplies excitation current 40 to the body of patient 10, and measures the response. Voltage 42 is supplied to an amplifier 52, which finds the voltage difference 54 between electrodes 14 and 16. Amplifier 52 may also perform some filtering of noise from the input signal.

Amplifier 52 is the gateway between programmable impedance system 34 and interface 22. Accordingly, excitation current 40 is channeled through amplifier 52. In addition, amplifier 52 may provide protection to programmable impedance system 34 from electrical surges.

Programmable filter 56 receives voltage signal 54. Programmable filter 56 may be a band pass filter with a variable center frequency. Controller 48 selects the center frequency and supplies the center frequency to programmable filter 56. Although controller 48 may also adjust the bandwidth of programmable filter 56, the bandwidth is ordinarily narrow, to reject substantially all frequencies except the frequency of excitation current 40. When controller 48 supplies the selected frequency to programmable drive 46, controller 48 also supplies a corresponding center frequency to programmable filter 56.

A detector 58 receives filtered signal 60. Detector 58 recovers the signal or signals that represent the measure of impedance. The signals may include, for example, a magnitude signal and a phase signal, from which the resistive and reactive components of the impedance may be found. Alternatively, the signals may express the impedance as a real part and an imaginary part. In general, the measured impedance is equal to measured voltage 54 divided by applied excitation current 40, where voltage 54 and current 40 are complex.

Detector 58 may be tuned by controller 48 to recover the signals at the frequency of excitation current 40. Recovered signals 62 may be converted to digital signals 64 by analog-to-digital (A/D) converter 66 for processing or transmission by controller 48. Controller 48 may relay the measured impedance to other components of defibrillator 12. In particular, the impedance measured by programmable impedance system 34 may be used by microprocessor 26 to select the amount of energy to be stored in energy storage device 24. In a typical application, microprocessor 26 controls charging circuit 28 to increase capacitor charge voltage of energy storage device 24 to a specified level, so that a desired dosage of energy may be delivered to patient 10.

FIG. 2 shows an exemplary logical relationship among the components of programmable impedance system 34, but is not limited to any particular hardware or software implementation. For example, some components, such as programmable filter 56 and detector 58, may be realized as analog components, digital components, or a combination of analog and digital components. A/D converter 66 may be located so as to convert analog signals to digital signals where needed.

Furthermore, programmable impedance system 34 may include additional components that are not shown in FIG. 2, such as a bandpass filter to shape and remove noise from excitation current 40. Programmable impedance system 34 may also exclude components that shown in FIG. 2. The functions of controller 48, for example, may be performed by microprocessor 26. The invention encompasses all of these variations.

Figure 3:
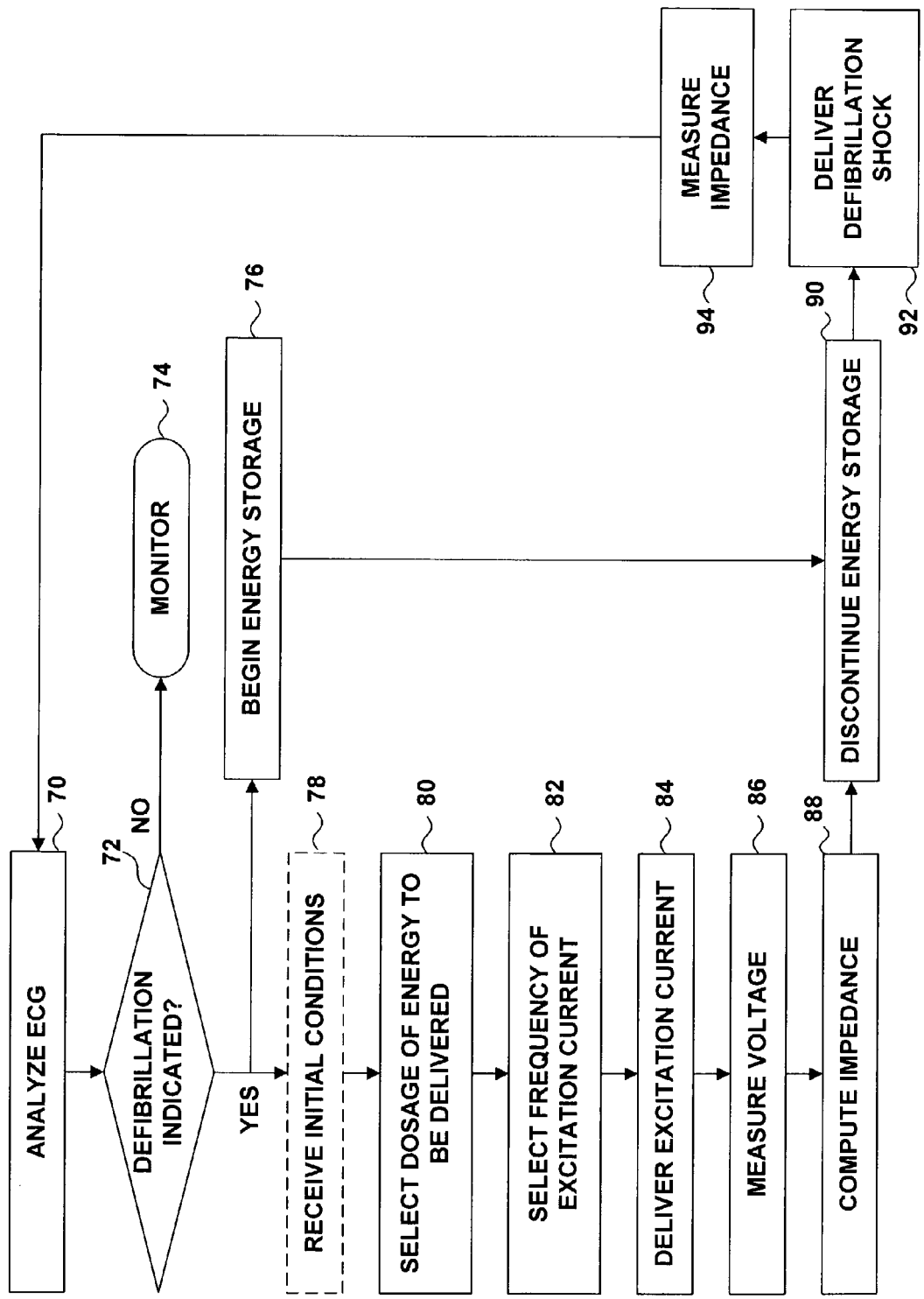
FIG. 3 is a flow diagram illustrating an exemplary operation of a defibrillator.

FIG. 3 is a flow diagram illustrating an exemplary operation of defibrillator 12. Upon placement of electrodes 14 and 16 on the chest of patient 10, microprocessor 26 analyzes ECG signals from the heart of patient 10 (70). Microprocessor 26 determines whether patient 10 suffers from a condition that requires a defibrillation shock, based upon the ECG signals (72). If defibrillation is not indicated, no shock is delivered, but monitoring of the ECG may continue (74).

If defibrillation is indicated, the defibrillation sequence starts. In particular, microprocessor 26 controls charging circuit 28 to begin charging energy storage device 24 (76). Microprocessor 26 also selects a dosage of energy to be delivered to patient 10 (80). For the first defibrillation shock, the dosage delivered may be a default dosage of energy, such as 200 joules. The dosage selected may also depend upon initial conditions supplied to defibrillator 12 by an operator (78), such as the sex, approximate age or approximate weight of patient 10.

Delivery of the selected dosage of energy to patient 10 depends upon the voltage developed across electrodes 14 and 16, which is a function of the capacitor charge voltage of energy storage device 24. Delivery of the selected dosage of energy to patient 10 also depends upon the impedance of the body of patient 10. Accordingly, programmable impedance system 34 proceeds to measure the impedance of patient 10. Microprocessor 26 or programmable impedance system 34 selects a frequency for excitation current 40 (82) and programmable impedance system 34 delivers excitation current 40 to patient 10 via electrodes 14 and 16 (84).

The frequency selected for excitation current 40 is a function of the selected dosage of energy to be delivered to patient 10. Techniques for selection of the frequency of excitation current 40 will be described below. When programmable impedance system 34 applies excitation current 40 to patient 10 at the selected frequency and measures the voltage that results from application of excitation current 40 (86), programmable impedance system 34 obtains a reasonably accurate measurement of the impedance that patient 10 will exhibit and that defibrillator 12 will see when delivering the energy in a defibrillation shock (88).

Microprocessor 26 charges energy storage device 24 to a voltage that will deliver the selected dosage of energy, taking into consideration the measured impedance of patient 10 (90). When energy storage device 24 has stored sufficient energy, defibrillator 12 delivers a defibrillation shock (92). The electrical pulse may be modulated to improve the delivery of energy depending on the measured impedance of patient 10. As noted above, modulation may include regulation of the shape of the waveform of the electrical pulse and the duration of the pulse.

In addition to measuring impedance prior to delivery of the defibrillation shock, defibrillator 12 may measure impedance during delivery of the defibrillation shock as well (94). This measurement may help gauge the accuracy of the impedance measurement made by observing the response to application of excitation current (84, 86, 88).

After delivery of a defibrillation shock, the ECG of the patient is measured again (70) to evaluate the efficacy of the shock (72). In some cases, the heart of patient 10 fails to respond to a defibrillation shock, and another shock, often delivering an increased dosage of energy, is indicated. Programmable impedance system 34 measures the impedance of patient 10 again by selecting an excitation current frequency as a function of the new dosage (82), delivering the excitation current (82) and measuring the voltage across electrodes 14 and 16 (86).

Figure 4:
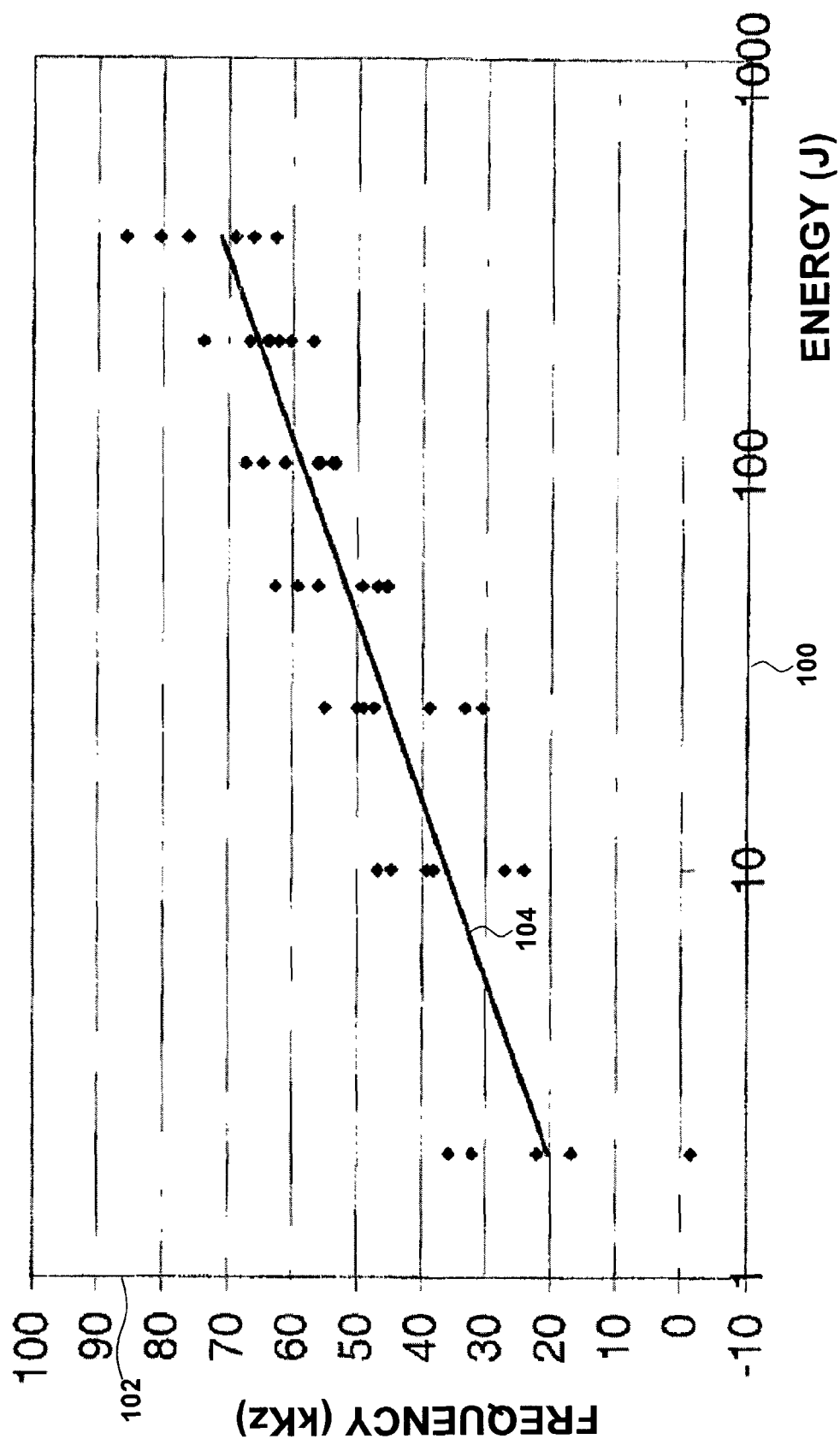
FIG. 4 is a chart illustrating an exemplary technique for selection of frequency of an excitation current as a function of an energy dosage to be delivered to a patient.

FIG. 4 is a chart illustrating an exemplary technique for selection of frequency of excitation current 40 as a function of the dosage of energy to be delivered to patient 10. The horizontal scale 100 shows the energy to be delivered, in joules. The horizontal scale 100 is logarithmic. The vertical scale 102 represents the frequency of excitation current 40, in kilohertz.

The data points in the chart have been derived by experimentation. In particular, the data points represent the excitation current frequencies that were used to measure patient impedance for different dosages of energy, with the least amount of error. The equation of the "best fit" line 104 of the data points is $9.7876 * \ln(x) + 13.56$, with an R-squared value of 0.7891. The data points may also be approximated with a curve other than a straight line. In general, for a lower energy defibrillation shock, a lower excitation current frequency results in a more accurate impedance measurement, and consequently a more accurate delivery of energy to patient 10.

Upon selecting a dosage of energy for delivery, microprocessor 26 or programmable impedance system 34 may select an excitation current frequency by applying the equation illustrated in FIG. 4. Alternatively, microprocessor 26 or programmable impedance system 34 may select an excitation current frequency by consulting a lookup table that maps defibrillation energy to excitation frequency.

The excitation current frequency may also be a function of factors in addition to defibrillation energy, such as the sex, age or body mass of patient 10, the impedance measurement obtained during delivery of a previous defibrillation shock, the number of defibrillation shocks previously delivered, or the shape and duration of the waveform of the electrical pulse. Accordingly, a chart, such as the chart shown in FIG. 4, need not include a single curve, but may include a family of curves. Similarly, there may be a family of equations or lookup tables that relate an energy dosage and an excitation current frequency.

Figure 5:
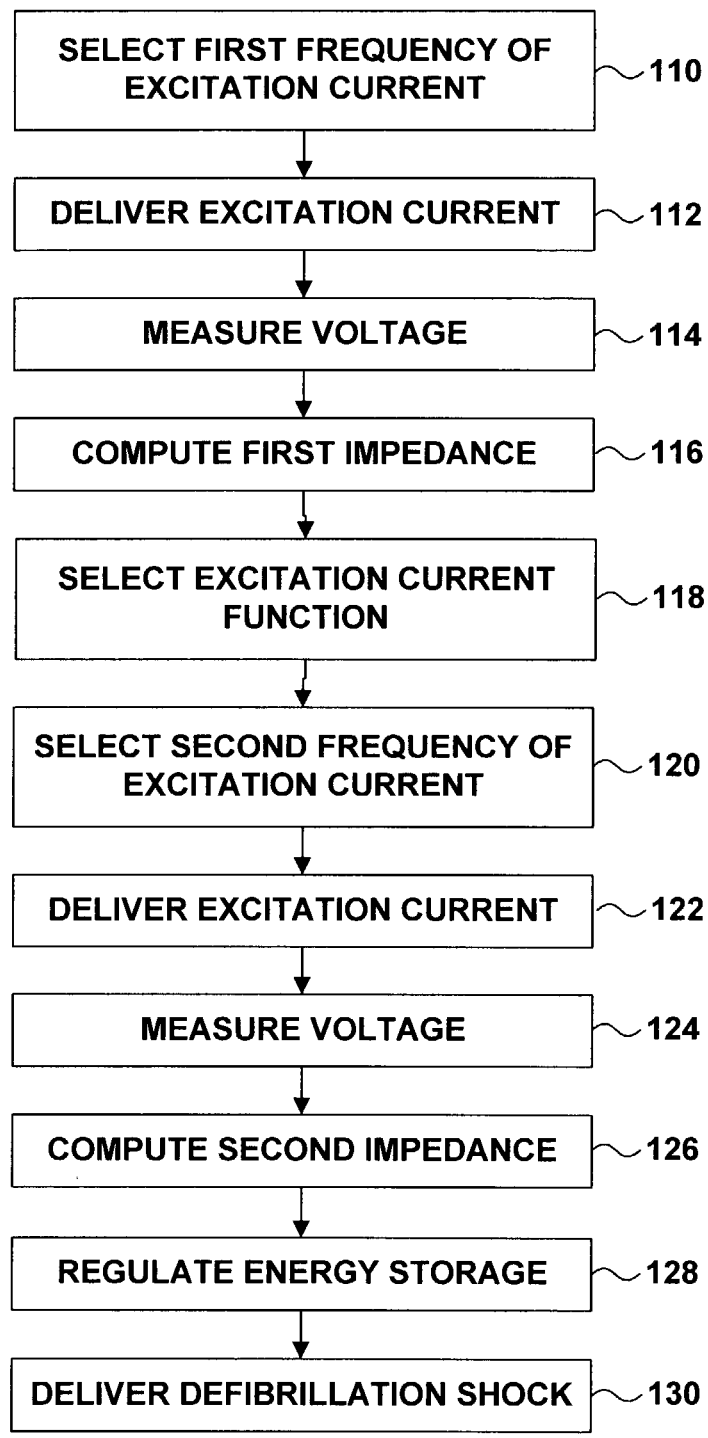
FIG. 5 is a flow diagram illustrating another technique for selection of frequency of an excitation current as a function of a dosage to be delivered to a patient.

FIG. 5 illustrates a technique in which programmable impedance system 34 may select an excitation current frequency as a function of at least one other measurement of impedance. A first excitation current frequency is selected (110). The first excitation current frequency may be a standard or default frequency, and need not be a function of the dosage to be delivered to patient 10. A first excitation current is delivered at the first frequency (112). The voltage that results from application of the excitation current at the first frequency is measured (122), and a first impedance is computed (124). Based upon the first measured impedance, an excitation current function is selected. An excitation current function may be, for example, a curve, equation or lookup table that relates excitation current frequency to an energy or current dosage. Microprocessor 26 or programmable impedance system 34 may, for example, select one curve when the measured first impedance is high and a different curve when the measured first impedance is low.

Microprocessor 26 or programmable impedance system 34 selects a frequency for the excitation current according to the dosage and the excitation current function (120). A second excitation current at the selected frequency is delivered (122), and a second impedance is measured (124, 126). The second measured impedance may represent an estimate of the impedance that defibrillator 12 is likely to see when delivering the dosage. Microprocessor 26 may regulate the charging of energy storage device 24 to a voltage that will deliver the desired dosage, taking into consideration the measured impedance of patient 10 (128). Defibrillator 12 may thereafter deliver a defibrillation shock having the desired dosage (130). In this way, one or more additional impedance measurements may be used to obtain a more accurate selection of the excitation current frequency that will measure the impedance defibrillator 12 will see when delivering a dosage to patient 10.

The additional impedance measurements may be used for other purposes as well. For example, the difference between the first and second impedance measurements may be indicative of the body mass of patient 10. The difference between the first and second impedance measurements may also indicate whether defibrillator 12 is coupled to a patient. At times, defibrillator 12 may be coupled to a test device to determine whether defibrillator 12 is operating properly. A typical test device includes a resistive element, such as a high-power fifty ohm resistor, to simulate the patient. The simulation is somewhat inaccurate, however, because the impedance of a patient's body typically includes both resistive and reactive components, while the test device has a negligible reactive component. By measuring a first and second impedance, therefore, defibrillator 12 may be able to recognize that the delivery of a dosage of energy or current is a test rather than an actual defibrillation. When defibrillator 12 detects that a test is underway, defibrillator 12 may automatically enter a testing mode. When in testing mode, defibrillator 12 may, for example, prevent data becoming stored in memory 36, thereby reducing the risk of accidentally overwriting actual patient data with test data, or may identify the stored data as test data.

Single or multiple impedance measurements, e.g., by continuous sampling, may be useful in many other contexts as well. For example, the measurement of impedance is also affected by the motion of patient 10. When the patient is not moving voluntarily or being moved by others (e.g., by administration of cardiopulmonary resuscitation), the changes of impedance at a fixed excitation current frequency may be indicative of involuntary motion, such as respiration. In other words, when electrodes 14 and 16 are first applied to patient 10, defibrillator 12 may measure both the ECG and the respiration rate of patient 10.

Impedance measurements may also indicate whether an electrode is properly affixed to the skin of patient 10. If an electrode comes loose, then the measured impedance will increase dramatically. An I/O device 32 may advise the operator that an electrode has come loose. The above uses of impedance measurements are complementary and are nonexclusive. The invention may operate in harmony with impedance measurements made for any other purpose.

The invention can provide one or more advantages. In particular, the invention provides techniques for more accurate, and therefore more effective, delivery of energy to a patient. By selecting an excitation current frequency as a function of the energy to be delivered, the defibrillator may obtain a more accurate estimate of the impedance the patient may exhibit when the defibrillator delivers the defibrillation shock. As a result, the energy storage device may be charged more closely to a proper voltage level, and the shape and duration of the defibrillation pulse may be adapted to the impedance of the patient. An additional benefit is that the range of tolerance for the components such as the energy storage device is reduced, thereby saving construction costs.

As mentioned above, the invention is not limited to dosages quantified according to units of energy. Dosages may also be quantified according to units of current delivered in a defibrillation shock. The techniques described above may also be employed to select an excitation current frequency as a function of the defibrillation current to be delivered.

Various embodiments of the invention have been described. These embodiments are illustrative of the practice of the invention. Various modifications may be made without departing from the scope of the claims. For example, programmable impedance system 34 may measure impedance by any of a number of impedance-measuring techniques. The invention is not limited to measuring impedance by measuring a voltage. Nor is the invention limited to an excitation current of a single frequency, but encompasses embodiments in which an excitation current includes multiple frequency components. These and other embodiments are within the scope of the following claims.

The invention claimed is:

1. A method comprising:
    identifying a dosage of at least one defibrillation shock parameter selected for a patient for a pending defibrillation shock to be delivered to the patient with a defibrillator,
    wherein the defibrillation shock parameter is selected from the following group: energy and defibrillation current;
    after identifying the dosage, selecting a frequency of an excitation current as a function of the identified dosage;
    applying the excitation current to the patient at the selected frequency;
    measuring an impedance of the patient by measuring a response of the patient to application of the excitation current;
    delivering the defibrillation shock to the patient; and
    modulating the defibrillation shock based on the measured impedance to deliver the identified dosage to the patient.

2. The method of claim 1, wherein measuring an impedance of the patient comprises measuring an impedance of the patient by measuring a magnitude and a phase of the response of the patient to application of the excitation current.

3. The method of claim 1, wherein measuring an impedance comprises measuring a first impedance, the method further comprising measuring a second impedance of the patient by measuring a response of the patient to delivery of the defibrillation shock.

4. The method of claim 1, further comprising selecting the dosage as a function of at least one patient parameter,
    wherein the patient parameter is selected from the following group: sex, age and body mass.

5. The method of claim 1, further comprising selecting the dosage as a function of a dosage of at least one defibrillation shock parameter delivered to the patient in a previous defibrillation shock,
    wherein the defibrillation shock parameter is selected from the following group: energy and defibrillation current.

6. The method of claim 1, wherein selecting the frequency of the excitation current as a function of the dosage to be delivered to the patient with the defibrillator comprises selecting the frequency of the excitation current according to a formula that relates frequency values to dosage values.

7. The method of claim 1, wherein selecting the frequency of the excitation current as a function of the dosage to be delivered to the patient with the defibrillator comprises selecting the frequency from a lookup table.

8. The method of claim 1, further comprising storing energy in an energy storage device prior to delivery of the dosage to the patient.

9. The method of claim 1, wherein the frequency is a first frequency, the dosage is a first dosage, and measuring an impedance comprises measuring a first impedance, the method further comprising:

selecting a second dosage to be delivered to the patient with the defibrillator;

selecting a second frequency of the excitation current as a function of the second dosage:

applying the excitation current to the patient at the second selected frequency; and measuring a second impedance of the patient by measuring a response of the patient to application of the excitation current at the second selected frequency.

10. A defibrillator comprising:

a processor that selects a dosage of at least one defibrillation shock parameter for a pending defibrillation shock to be delivered to a patient, wherein the defibrillation shock parameter is selected from the following group: energy and defibrillation current;

a current source that generates an excitation current at a selectable frequency, the frequency of the excitation current being selected after dosage selection and as a function of the selected dosage;

an impedance measuring circuit that measures impedance of the patient as a function of a response of the patient to application of the excitation current to the patient, wherein the processor modulates the defibrillation shock based on the measured impedance to deliver the selected dosage to the patient; and at least two electrodes that deliver the defibrillation shock to the patient.

11. The defibrillator of claim 10, wherein the impedance measuring circuit comprises a voltage measurement device.

12. The defibrillator of claim 10, further comprising at least two electrodes that deliver the excitation current to the patient.

13. The defibrillator of claim 12, further comprising an impedance measuring circuit that measures the voltage across the electrodes and measures the impedance as a function of the voltage and the excitation current.

14. The defibrillator of claim 10, further comprising an energy storage device that stores energy for the dosage to be delivered to the patient.

15. The defibrillator of claim 10, wherein the processor selects the frequency of the excitation current as a function of the selected dosage.

16. The defibrillator of claim 10, wherein the current source generates the excitation current at a frequency selectable from at least three frequencies.

* * * * *

UNITED STATES PATENT AND TRADEMARK OFFICE
CERTIFICATE OF CORRECTION

PATENT NO. : 8,417,327 B2
APPLICATION NO. : 10/176705
DATED : April 9, 2013
INVENTOR(S) : Chapman et al.

Page 1 of 1

It is certified that error appears in the above-identified patent and that said Letters Patent is hereby corrected as shown below:

In the Claims

Claim 9, Column 11, Line 4, the ":" should be replaced with --;--

Signed and Sealed this
Fifteenth Day of October, 2013

Teresa Stanek Rea
*Deputy Director of the United States Patent and Trademark Office*